US009736464B2

(12) United States Patent
Takao et al.

(10) Patent No.: US 9,736,464 B2
(45) Date of Patent: Aug. 15, 2017

(54) MICROSCOPE VIDEO PROCESSING DEVICE AND MEDICAL MICROSCOPE SYSTEM

(71) Applicant: ALLM INC., Tokyo (JP)

(72) Inventors: Hiroyuki Takao, Tokyo (JP); Yuichi Murayama, Tokyo (JP); Harunobu Endo, Tokyo (JP); Teppei Sakano, Tokyo (JP); Shogo Kaku, Kanagawa (JP)

(73) Assignee: ALLM INC., Tokyo (JP)

( * ) Notice: Subject to any disclaimer, the term of this patent is extended or adjusted under 35 U.S.C. 154(b) by 0 days.

(21) Appl. No.: 15/038,612

(22) PCT Filed: Nov. 21, 2014

(86) PCT No.: PCT/JP2014/080894
§ 371 (c)(1),
(2) Date: May 23, 2016

(87) PCT Pub. No.: WO2015/080042
PCT Pub. Date: Jun. 4, 2015

(65) Prior Publication Data
US 2016/0295199 A1    Oct. 6, 2016

(30) Foreign Application Priority Data
Nov. 29, 2013 (JP) ................. 2013-246968

(51) Int. Cl.
*H04N 13/02* (2006.01)
*G02B 21/36* (2006.01)
(Continued)

(52) U.S. Cl.
CPC ......... *H04N 13/0292* (2013.01); *A61B 90/20* (2016.02); *A61B 90/36* (2016.02);
(Continued)

(58) Field of Classification Search
CPC ... A61B 2090/365; A61B 90/20; A61B 90/36; G02B 21/0012; G06T 2207/10081;
(Continued)

(56) References Cited

U.S. PATENT DOCUMENTS

2001/0027272 A1* 10/2001 Saito ............... A61B 1/0005
600/426
2003/0069471 A1* 4/2003 Nakanishi ........ A61B 1/0005
600/101
(Continued)

FOREIGN PATENT DOCUMENTS

JP    2004151490 A2    5/2004
JP    2007007041 A2    1/2007
(Continued)

OTHER PUBLICATIONS

Japanese Office Action issued on May 13, 2015 for the corresponding Japanese Patent Application No. 2013-246968.
(Continued)

*Primary Examiner* — Md Haque
(74) *Attorney, Agent, or Firm* — Rankin, Hill & Clark LLP

(57) ABSTRACT

The present invention is intended to convert a video input from a surgical microscope into a three-dimensional video. A microscope video processing device 100 includes: a microscope video acquisition unit that acquires a microscope video output from an surgical microscope 200; a video conversion unit that converts the microscope video acquired by the microscope video acquisition unit into a three-dimensional video; a surgical instrument position determination unit that determines the position of a surgical instrument in the three-dimensional video converted by the video conversion unit; a distance calculation unit that calculates a distance between a preset patient's preset surgery target region and the position of the surgical instrument deter-
(Continued)

mined by the surgical instrument position determination unit; and a video output unit that outputs to a display unit an output video in which distance information indicative of the distance calculated by the distance calculation unit is displayed in the three-dimensional video.

10 Claims, 7 Drawing Sheets

(51) Int. Cl.
*G02B 21/00* (2006.01)
*A61B 90/20* (2016.01)
*A61B 90/92* (2016.01)
*G06T 19/00* (2011.01)
*A61B 90/00* (2016.01)

(52) U.S. Cl.
CPC .......... *A61B 90/92* (2016.02); *G02B 21/0012* (2013.01); *G02B 21/367* (2013.01); *G06T 19/006* (2013.01); *A61B 2090/365* (2016.02); *G06T 2207/10081* (2013.01); *G06T 2207/10088* (2013.01); *H04N 2213/006* (2013.01)

(58) Field of Classification Search
CPC ...... G06T 2207/10088; H04N 13/0292; H04N 2213/006
See application file for complete search history.

(56) References Cited

U.S. PATENT DOCUMENTS

2008/0004603 A1\* 1/2008 Larkin .................. B25J 9/1692
606/1
2015/0051617 A1 2/2015 Keiho

FOREIGN PATENT DOCUMENTS

JP 2009542362 12/2009
WO 2013145730 A1 10/2013

OTHER PUBLICATIONS

International Search Report dated0 Mar. 3, 2015 filed in PCT/JP2014/080894.

\* cited by examiner

MICROSCOPE VIDEO PROCESSING DEVICE AND MEDICAL MICROSCOPE SYSTEM

TECHNICAL FIELD

The present invention relates to a microscope video processing device and a medical microscope system.

BACKGROUND ART

There is known a surgical microscope. The surgical microscope is an electronic image stereoscopic microscope using an imaging element that subjects an observation image to image processing for a natural stereoscopic effect (refer to Patent Literature 1).

CITATION LIST

Patent Literature

Patent Literature 1: JP-A-2004-151490

SUMMARY OF THE INVENTION

Problems to be Solved by the Invention

The conventional surgical microscopes display stereoscopic microscope images of an observation target but have a problem in performing surgical operations while viewing microscope images that it is difficult for a surgeon to get a sense of distance between a patient's surgery target region and a surgical instrument held by them in the displayed image.

Solution to Problem

According to a first mode of the present invention, a microscope video processing device includes: a microscope video acquisition unit that acquires a microscope video output from an surgical microscope at a predetermined frame rate; a video conversion unit that converts the microscope video acquired by the microscope video acquisition unit into a three-dimensional video; a surgical instrument position determination unit that, in a surgical instrument with a handle portion to which color-coded markings are applied to discriminate between the front end side and back end side of the surgical instrument in the microscopic video acquired by the microscope video acquisition unit, determines the position of a marking for identifying the foremost end position as front end position of the surgical instrument, and converts a coordinate value of the determined front end position in the microscope video into a coordinate value in the three-dimensional video to determine the front end position of the surgical instrument in the three-dimensional video converted by the video conversion unit; a distance calculation unit that calculates a distance between a preset patient's surgery target region and the front end position of the surgical instrument determined by the surgical instrument position determination unit; and a video output unit that outputs to a display unit an output video in which distance information indicative of the distance calculated by the distance calculation unit is displayed in the three-dimensional video.

According to a second mode of the present invention, in the microscope video processing device of the first mode, the video conversion unit creates a three-dimensional CT image by overlaying CT slice images of the patient's surgery target region shot before the surgery, creates a three-dimensional MRI image by overlaying MRI slice images of the patient's surgery target region shot before the surgery, aligns and superimposes the three-dimensional CT image, the three-dimensional MRI image, and a prepared three-dimensional model image of the surgery target region to create a three-dimensional image of the patient's surgery target region, and aligns and superimposes the three-dimensional image of the patient's surgery target region and frames of the microscope video acquired by the microscope video acquisition unit to convert the microscope video into the three-dimensional video.

According to a third mode of the present invention, in the microscope video processing device of the first or second mode, when the coordinate value of the front end position of the surgical instrument cannot be determined because the front end position of the surgical instrument is not seen in the microscope video acquired by the microscope video acquisition unit, the surgical instrument position determination unit estimates the coordinate value of the front end position of the surgical instrument based on part of the surgical instrument seen in the microscope video and a predetermined length of the surgical instrument.

According to a fourth mode of the present invention, in the microscope video processing device of any one of the first to three modes, the distance calculation unit calculates a straight-line distance, a horizontal distance, a vertical distance, and a distance in a depth direction between the surgery target region and the front end position of the surgical instrument, based on the preset coordinate value of the surgery target region in the three-dimensional video and the coordinate value of the front end position of the surgical instrument determined by the surgical instrument position determination unit.

According to a fifth mode of the present invention, the microscope video processing device of any one of the first to fourth modes further includes a surgical target region position information display unit that displays surgical target region position information indicating the position of the surgical target region in the three-dimensional video.

According to a sixth mode of the present invention, the microscope video processing device of any one of the first to fifth modes further includes a risky region position information display unit that displays risky region position information indicating risky regions at risk for injury on the periphery of the surgical target region in the three-dimensional video.

According to a seventh mode of the present invention, a medical microscope system includes: the microscope video processing device of any one of the first to sixth modes; and a surgical microscope that is connected to the microscope video processing device to input a microscope video to the microscope video processing device at a predetermined frame rate.

Advantageous Effects of the Invention

According to the present invention, the distance information indicative of the distance between the patient's surgical target region and the surgical instrument is displayed in the three-dimensional video. This allows a surgeon to recognize the correct distance between the patient's surgery target region and the surgical instrument held by them.

DESCRIPTION OF EMBODIMENTS

Figure 1:
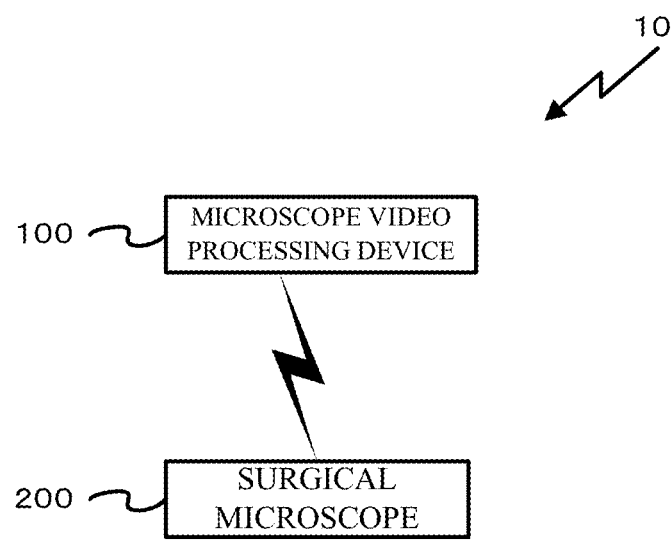
FIG. 1 is a block diagram illustrating a configuration of an embodiment of a medical microscope system 10.

FIG. 1 is a block diagram illustrating a configuration of an embodiment of a medical microscope system 10. The medical microscope system 10 is composed of a microscope video processing device 100 and a surgical microscope 200. In the embodiment, the microscope video processing device 100 and the surgical microscope 200 are connected together via a connection cable or through wireless communications, for example. The wireless communications may be performed using a publicly known communication technique such as a wireless LAN or Bluetooth (registered trademark).

The surgical microscope 200 is composed of a mount part including an arm and a microscope part that is attached to a tip of the arm to shoot a subject under magnification. The arm has predetermined ranges of movement in horizontal, vertical, and rotational directions to change arbitrarily the position of the microscope part. The microscope part includes an imaging part composed of an imaging element, lenses, and the like. The microscope part drives a zoom lens to magnify an observation target image and drives a focus lens to focus on the observation target, and acquires an image of the observation target. In the embodiment, the microscope part can acquire the image at a predetermined frame rate and output a video of the observation target. The structure and functions of surgical microscope are publicly known and thus detailed descriptions thereof are not provided here.

The microscope video processing device 100 is a device that processes a video input from the surgical microscope 200. The microscope video processing device 100 may be an information processing device such as a personal computer or a server device, for example. Installing a software application for processing a video input from the surgical microscope 200 onto the information processing device allows the information processing device to execute processes described later.

Figure 2:
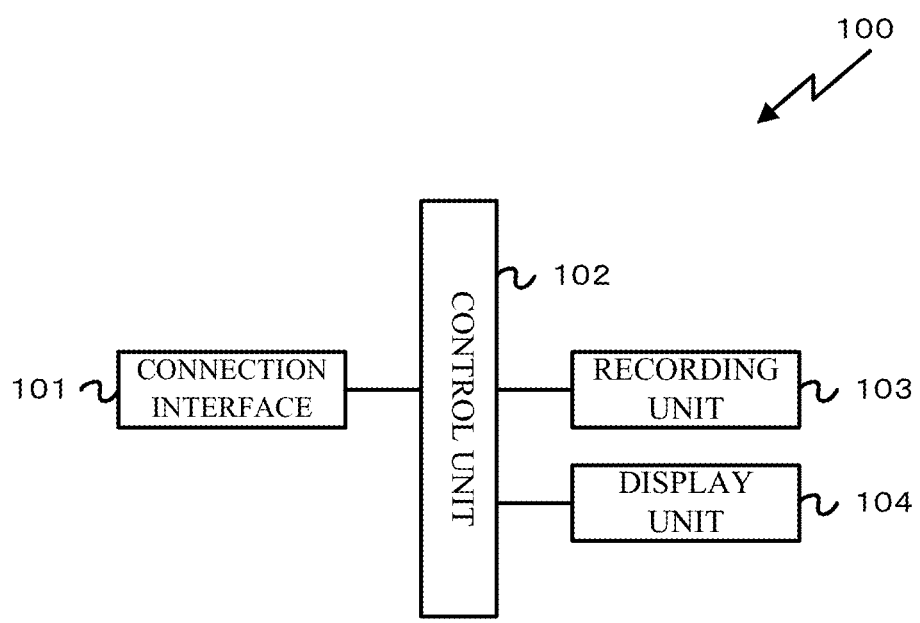
FIG. 2 is a block diagram illustrating a configuration of an embodiment of a microscope video processing device 100.

FIG. 2 is a block diagram illustrating a configuration of an embodiment of the microscope video processing device 100 as a personal computer. The microscope video processing device 100 includes a connection interface 101, a control unit 102, a recording unit 103, and a display unit 104.

The connection interface 101 is an interface for connecting the microscope video processing device 100 to the surgical microscope 200. The connection interface 101 may be an interface for wired connection with the surgical microscope 200, or an interface for wireless connection with the surgical microscope 200, for example.

The control unit 102 is composed of a CPU, a memory, and other peripheral circuits, which controls the entire microscope video processing device 100. The memory constituting the control unit 102 is a volatile memory such as an SDRAM, for example. The memory is used as a work memory for the CPU to develop a program at the time of its execution, or a buffer memory for temporarily recording data. For example, the data read via the connection interface 101 is temporarily recorded in the buffer memory.

The recording unit 103 is a recording unit that records various data accumulated in the microscope video processing device 100, data for programs to be executed by the control unit 102, and others. The recording unit 103 may be an HDD (hard disk drive) or an SSD (solid state drive), or the like, for example. The program data of the software application for processing a video input from the surgical microscope 200 described above is recorded in the recording unit 103. The program data recorded in the recording unit 103 is saved in a recording medium such as a CD-ROM or a DVD-ROM or is provided via a network and acquired by an operator, and is installed onto the recording unit 103 so that the control unit 102 can execute the program.

The display unit 104 is a display unit that displays the information output from the control unit 102. The display unit 104 may be a liquid crystal monitor or the like, for example.

In the medical microscope system 10 of the embodiment, the control unit 102 of the microscope video processing device 100 performs processes described below on the video input from the surgical microscope 200 via the connection interface 101.

In the embodiment, to perform surgery using the surgical microscope 200, the operator of the microscope video processing device 100 records in advance in the recording unit 103 CT slice images of the patient's surgery target region shot before the surgery, MRI slice images of the patient's surgery target region shot before the surgery, and a three-dimensional model image of the surgical target region.

The CT slice images of the surgery target region are a plurality of CT images obtained by shooting the cross section of the patient's surgical target region and its periphery in a predetermined slice thickness. The MRI slice images of the surgery target region are a plurality of MRI images obtained by shooting the cross section of the patient's surgery target region and its periphery in a predetermined slice thickness. The three-dimensional model image of the surgery target region is a three-dimensionally modeled image of the patient's surgery target region and its periphery. The three-dimensional model image of the region is generally created by a publicly-known method.

When the surgical microscope 200 starts to input a microscope video via the connection interface 101, the control unit 102 converts the input microscope video into a three-dimensional video by subjecting the frames of the microscope video to image processing to create a three-dimensional image. The process for converting the microscope video into the three-dimensional video executed by the control unit 102 will be described below.

The control unit 102 reads the CT slice images of the patient's surgery target region from the recording unit 103, and overlays the CT slice images to create a three-dimensional CT image of the patient's surgery target region. The control unit 102 also reads the MRI slice images of the patient's surgery target region from the recording unit 103, and overlays the MRI slice images to create a three-dimensional MRI image of the patient's surgery target region.

The control unit 102 reads the three-dimensional model image of the surgery target region from the recording unit 103, and aligns and superimposes the created three-dimensional CT image, three-dimensional MRI image, and three-dimensional model image to create a three-dimensional image of the patient's surgery target region. The three-dimensional CT image, the three-dimensional MRI image, and the three-dimensional model image are aligned by subjecting these images to publicly-known image processing such as binarization and labeling to extract characteristic shapes from the images, and overlaying these characteristic shapes.

The characteristic shapes to be overlaid may be the shapes of a blood vessel seen in the images, or the like. As a specific example, to perform surgery to cut open the sulcus Sylvius in the brain, the internal carotid artery is Y-shaped characteristically and thus the general shape of the internal carotid artery is registered in advance as a template image. The control unit 102 extracts shapes analogous to the shape of the internal carotid artery in the registered template image from the three-dimensional CT image, the three-dimensional MRI image, and the three-dimensional model image. The control unit 102 aligns and overlays the three-dimensional CT image, the three-dimensional MRI image, and the three-dimensional model image such that the extracted characteristic shapes of the internal carotid artery overlap one another, thereby creating a three-dimensional image to be represented by a XYZ coordinate system. However, this is a mere example. The characteristic shapes for use in alignment may be selected depending on the patient's surgery target region, such as extracting the characteristic shapes of anterior cerebral artery to perform surgery to cut open the longitudinal fissure of cerebrum, or extracting the characteristic shape of basilar artery or the posterior cerebral artery to perform surgery to cut open the bottom surface of the temporal lobe.

When the surgical microscope 200 starts to input the microscope video, the control unit 102 aligns and superimposes the frames of the microscope video input at a predetermined frame rate and the three-dimensional image of the patient's surgery target region created by the process described above to convert the two-dimensional microscope video into a three-dimensional video. The three-dimensional image and the frames of the microscope video can be aligned by extracting characteristic shapes such as the shapes of a blood vessel from the three-dimensional image and the frames of the microscope video and overlaying the characteristic shapes, as in the process described above.

The control unit 102 outputs the converted three-dimensional video to the display unit 104 for display. Accordingly, the surgeon or the like can perform surgery while recognizing the surgery target region in three dimensions.

The microscope video processing device 100 of the embodiment has the function of determining the position of the surgical instrument seen in the microscope video input from the surgical microscope 200 in the three-dimensional video, and displaying the distance between the patient's surgery target region and the surgical instrument in the three-dimensional video. The process executed by the control unit 102 to display the distance between the patient's surgery target region and the surgical instrument in the three-dimensional video will be described below. In the embodiment, the front end position of the surgical instrument is determined as the position of the surgical instrument.

Figure 3:
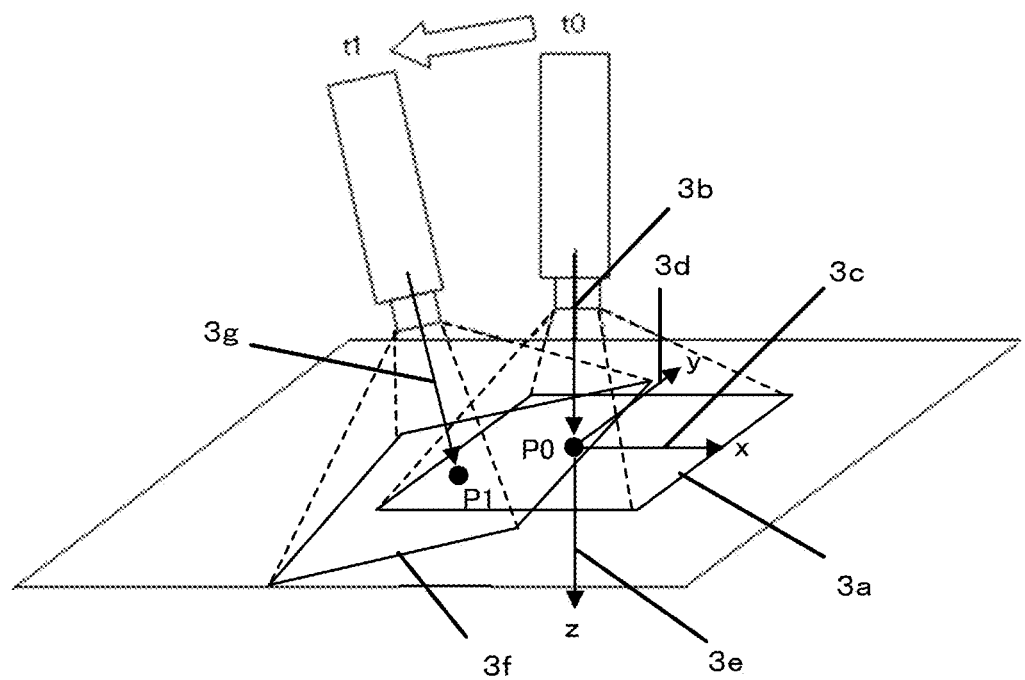
FIG. 3 is a diagram illustrating the relationship between a surgical microscope 200 and a microscope image plane.

First, to determine the front end position of the surgical instrument in the three-dimensional video, the control unit 102 performs a calibration process to align a microscope coordinate system in the microscope video input from the surgical microscope 200 and a display coordinate system in the three-dimensional video output to the display unit 104. In the calibration process, as illustrated in FIG. 3, the control unit 102 sets a three-dimensional coordinate system as the microscope coordinate system in which, on a microscope image plane 3a vertical to an optical axis 3b of the surgical microscope 200 at a position t0, an x axis 3c and a y axis 3d are taken with an origin point at a point P0 of intersection between the optical axis 3b and the microscope image plane 3a, and a z axis 3e is taken in the direction of the optical axis 3b of the surgical microscope 200.

In the embodiment, the control unit 102 aligns the display coordinate system and the microscope coordinate system by associating the origin point P0 (vP0, vV0, vM0) in the display coordinate system with the origin point P0 (rP0, rV0, rM0) in the microscope coordinate system relative to a coordinate value vP0 (vX0, vY0, vZ0) of the origin point P0 in the display coordinate system, a directional vector vV0 (vVx0, vVy0, vVz0) of the origin point P0 in the display coordinate system, and a display magnification vM0 of the origin point P0 in the display coordinate system, and a coordinate value rP0(rX0, rY0, rZ0) of the origin point P0 in the microscope coordinate system, a directional vector rV0 (rVx0, rVy0, rVz0) of the origin point P0 in the microscope coordinate system, and a display magnification rM0 of the origin point P0 in the microscope coordinate system. Specifically, the values (rP0, rV0, rM0) of the origin point P0 in the microscope coordinate system are associated with the values (vP0, vV0, vM0)=((0, 0, 0),(0, 0, 1), 1) of the origin point P0 in the display coordinate system.

Figure 4:
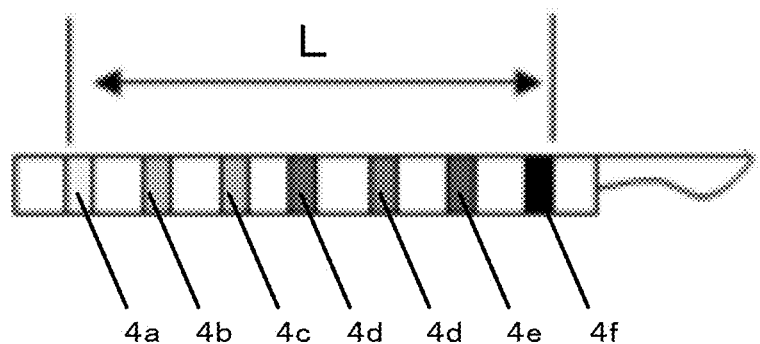
FIG. 4 is a schematic diagram of an example of markings applied to a surgical instrument.

The operator of the microscope video processing device 100 performs the calibration process and places the surgical instrument on the observation target surface 3a to determine the length of the surgical instrument in the microscope video during the calibration process. In the embodiment, as illustrated in FIG. 4, a plurality of markings 4a to 4f is applied to the surgical instrument. These markings are equally spaced at the handle portion of the surgical instrument, and are color-coded to discriminate the front end side and the back end side of the surgical instrument. For example, the marking 4a on the backmost end side is provided in a pale color, and the marking 4f on the foremost end side is provided in a dark color, and the markings 4b to 4e at the intermediate positions between the foregoing two are provided in colors becoming gradually darker from the marking 4b to the marking 4e. As a whole, the markings 4a to 4f have color gradations such that the colors become darker from the marking 4a to the marking 4f.

The control unit 102 extracts from the microscope video the markings on the surgical instrument placed on the observation target plane 3a, and determines the length from the marking 4a in the palest color to the marking 4f in the darkest color as length L of the surgical instrument. The control unit 102 records the determined length L of the surgical instrument in the memory. Accordingly, the calibration process and the surgical instrument length determination process are completed. The determined length L of the surgical instrument here refers to the length from the markings 4a to 4f applied to the handle portion and is different from the entire length of the surgical instrument. In the embodiment, however, the length L determined by the foregoing process is regarded as the length of the surgical instrument.

Next, a process for determining the front end position of the surgical instrument seen in the microscope video during surgery will be described. In the following description, the surgical microscope 200 is moved to a position t1 illustrated in FIG. 3 as an example. In this example, the shooting magnification of the surgical microscope 200 is the same as that in the calibration process. When the shooting magnification is changed, the control unit 102 performs the process taking the change in the shooting magnification into account.

Figure 5:
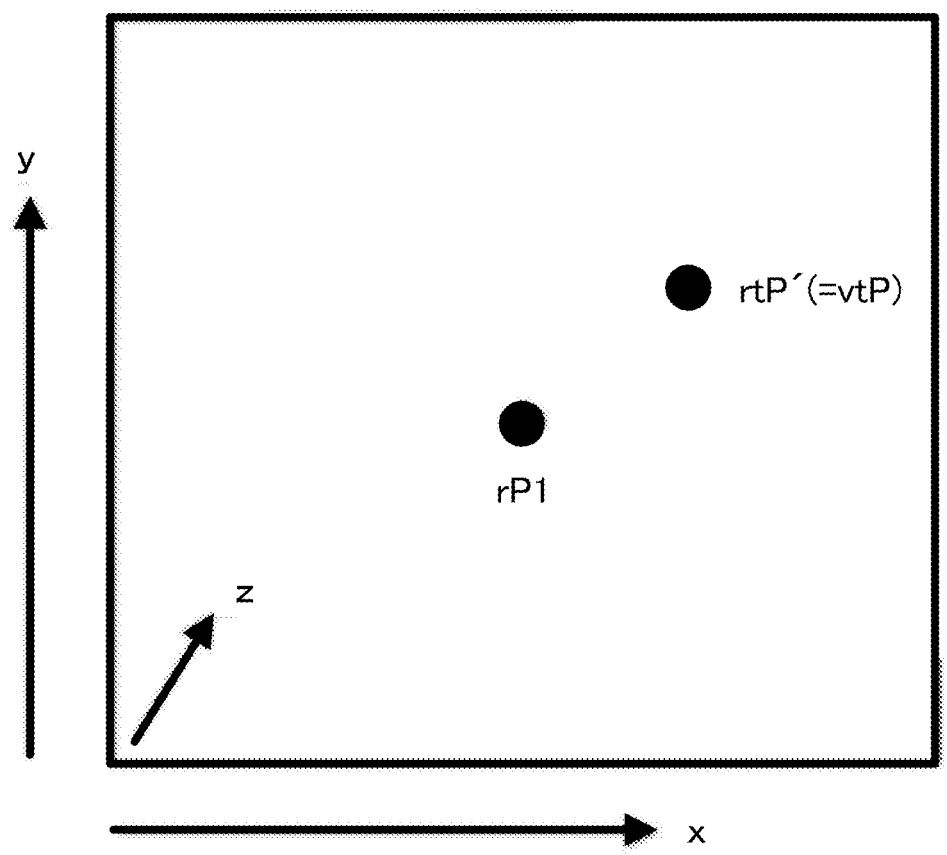
FIG. 5 is a diagram illustrating an example of a front end position of the surgical instrument in the microscope image plane.

In a coordinate system in which, on a microscope image plane $3f$ vertical to an optical axis $3g$ of the surgical microscope 200 at the position t1, an x axis and a y axis are taken in the microscope image plane $3f$ with an origin point at a point P1 of intersection between the optical axis $3g$ and the microscope image plane $3f$ and a z axis is taken in the direction of the optical axis $3g$ of the surgical microscope 200, the control unit 102 determines a coordinate value rP1 (rX1, rY1, rZ1) of the origin point P1. The control unit 102 also determines the position of the marking in the darkest color on the surgical instrument seen in the microscope video as the front end position of the surgical instrument, and determines a coordinate value rtP' (rtX', rtY', rtZ') of the front end position tP'. This clarifies the positional relation between the rP1 and rtP' in the microscope image plane $3f$ as illustrated in FIG. 5.

When the front end portion of the surgical instrument is seen in the microscope video, the control unit 102 can determine the position of the marking in the darkest color. However, when the surgical instrument is partially hidden behind the surgeon's hand or the like, the control unit 102 cannot determine the position of the marking in the darkest color and thus cannot determine the front end position of the surgical instrument. In this case, the control unit 102 estimates the front end position of the surgical instrument in such a manner as described below.

First, the control unit 102 determines the direction of change in the colors of the markings applied to the surgical instrument seen in the microscope video. Accordingly, the control unit 102 can determine that the direction in which the colors of the markings change from paler ones to darker ones indicates the direction toward the front end of the surgical instrument. Therefore, the control unit 102 can conclude that the front end position of the surgical instrument is hidden in the determined direction toward the front end.

The control unit 102 further determines the length of the surgical instrument seen in the microscope video, and estimates the front end position of the surgical instrument in the microscope video based on the determined length and the length L of the surgical instrument recorded in the memory in the foregoing process. Specifically, the control unit 102 estimates that the front end position of the surgical instrument in the microscope video is the position of the surgical instrument seen in the microscope video extended in the direction toward the front end until the length of the surgical instrument seen in the microscope video matches the length L of the surgical instrument recorded in the memory in the foregoing process. Accordingly, it is possible to determine the front end position of the surgical instrument even when the front end portion of the surgical instrument is hidden in the microscope video.

The control unit 102 converts the coordinate value rtP' (rtX', rtY', rtZ') of the determined front end position tP' of the surgical instrument into a coordinate value rtP (rtX, rtY, rtZ) in the microscope coordinate system. After that, the control unit 102 converts the coordinate value rtP (rtX, rtY, rtZ) in the microscope coordinate system into a coordinate value vtP (vtX, vtY, vtZ) in the display coordinate system, based on the results of alignment between the microscope coordinate system and the display coordinate system in the foregoing calibration process. Accordingly, the front end position of the surgical instrument in the display coordinate system can be determined.

The control unit 102 calculates the distance between the preset coordinate value of the surgery target region in the display coordinate system and the coordinate value vtP (vtX, vtY, vtZ) of the front end position of the surgical instrument in the display coordinate system determined in the foregoing process. The control unit 102 outputs the information of the calculated distance to the display unit 104 to display the distance information on the three-dimensional video. As for the coordinate value of the surgery target region in the display coordinate system, the operator of the microscope video processing device 100 registers in advance the coordinate value of the patient's surgery target region decided before the surgery.

Figure 6:
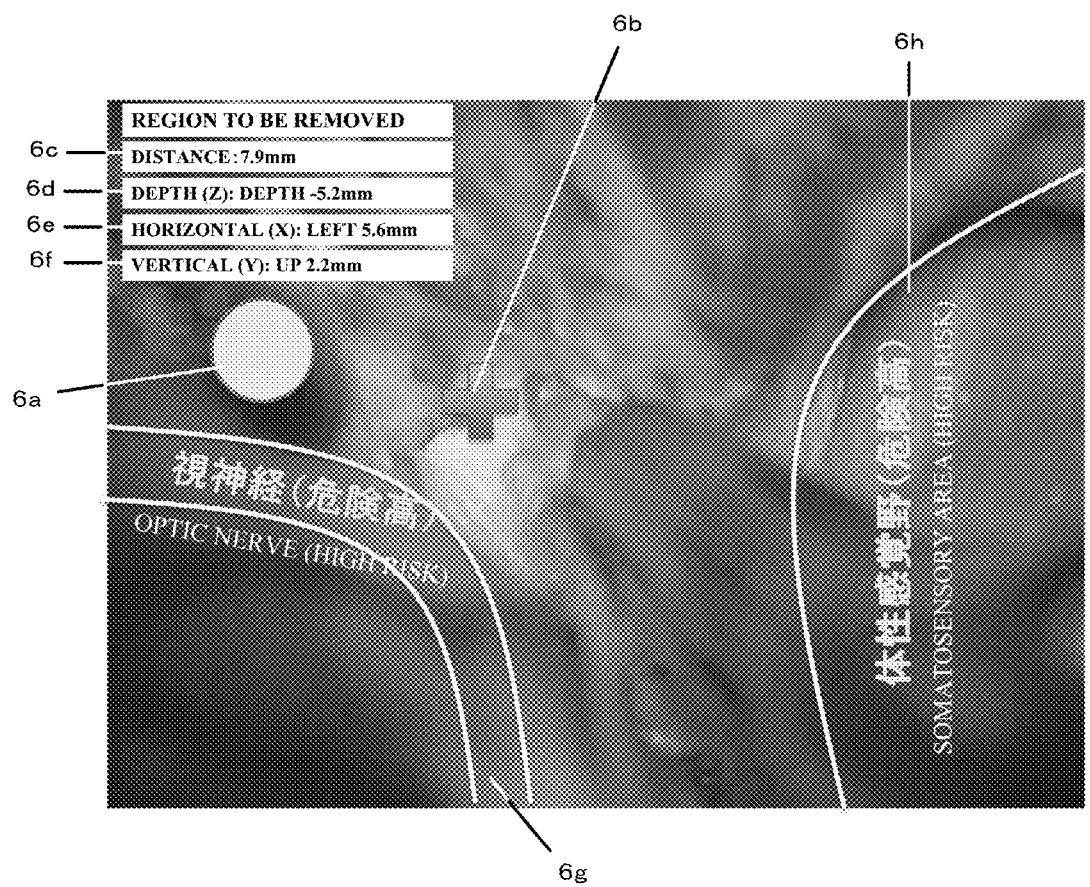
FIG. 6 is a diagram illustrating a specific display example of a three-dimensional video.

Accordingly, displayed in the three-dimensional video are: as information on the distance between a surgery target region 6*a* and a front end position 6*b* of the surgical instrument as illustrated in FIG. 6, a straight-line distance 6*c* between the two coordinates, a distance 6*d* in a depth direction, that is, in the Z-axis direction in the display coordinate system; a distance 6*e* in the horizontal direction, that is, in the X-axis direction in the display coordinate system; and a distance 6*f* in the vertical direction, that is, in the Y-axis direction in the display coordinate system. In addition, the surgery target region 6*a* is clearly shown in the three-dimensional video as illustrated in FIG. 6. Accordingly, the surgeon can recognize the surgery target region and the information on the distance between the current front end position of the surgical instrument and the surgery target region in the three-dimensional video.

In the embodiment, information indicating the position of risky regions requiring attention during the surgery is registered in the three-dimensional model image of the surgery target region. For example, when the surgery target region resides in the brain, region information for determining the positions of risky regions at risk for injury on the periphery of the surgery target region, such as the optic nerve, the auditory association area, and the somatosensory area is registered. Based on the information indicating the positions of the registered risky regions, the control unit 102 determines the risky regions in the display coordinate system, and displays the determined regions in the three-dimensional video. In the example of FIG. 6, a region 6*g* corresponding to the optic nerve and a region 6*h* corresponding to the somatosensory area are displayed. Accordingly, the surgeon can recognize the risky regions on the periphery of the surgery target region to reduce the risk involved in the surgery.

Figure 7:
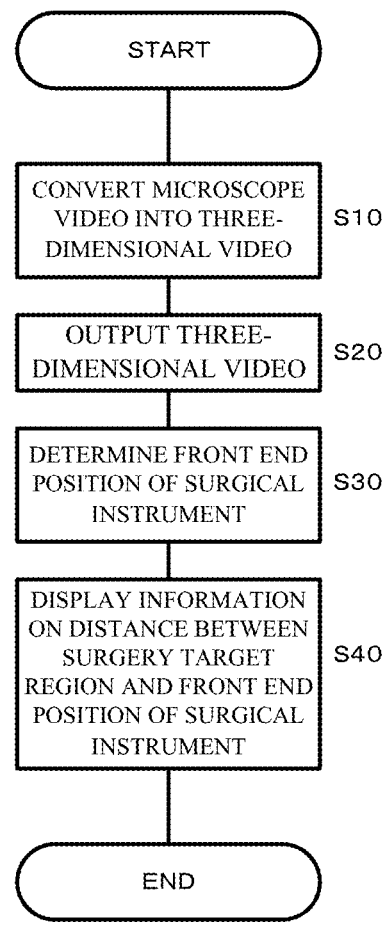
FIG. 7 is a flowchart of a process executed by the microscope video processing device 100.

FIG. 7 is a flowchart of a process executed by the microscope video processing device 100 of the embodiment. The process shown in FIG. 7 is executed by the control unit 102 as a program to be activated at the start of input of the microscope video from the surgical microscope 200. In the embodiment, the creation of the three-dimensional CT image and the three-dimensional MRI image, and the creation of the three-dimensional image of the patient's surgery target region using the three-dimensional CT image, the three-dimensional MRI image, and the three-dimensional model image are already completed.

At step S10, the control unit 102 aligns and superimposes the frames of the microscope video input at a predetermined frame rate and the three-dimensional image of the patient's surgery target region to convert the two-dimensional microscope video into the three-dimensional video as described above. The control unit 102 then moves to step S20.

At step S20, the control unit 102 outputs the three-dimensional video obtained by the conversion at step S10 to the display unit 104 for display. The control unit 102 then moves to step S30.

At step S30, the control unit 102 determines the front end position of the surgical instrument in the three-dimensional video as described above. The control unit 102 then moves to step S40.

At step S40, the control unit 102 displays the information on the distance between the surgery target region 6a and the front end position 6b of the surgical instrument in the three-dimensional video as illustrated in FIG. 6. At that time, the control unit 102 also displays the information 6g and 6h for determining the surgery target region 6a and the risky regions on the periphery of the surgery target region in the three-dimensional video. After that, the control unit 102 terminates the process.

According to the embodiment described above, the following advantageous effects can be obtained:

(1) The control unit 102 acquires the microscope video from the surgical microscope 200, converts the acquired microscope video into the three-dimensional video, determines the front end position of the surgical instrument in the three-dimensional video, calculates the distance between the preset patient's surgery target region and the determined front end position of the surgical instrument, and outputs to the display unit 104 the output video in which the information indicating the calculated distance is displayed in the three-dimensional video. Accordingly, the distance information indicating the distance between the patient's surgery target region and the position of the surgical instrument is displayed in the three-dimensional video. This allows the surgeon to recognize the correct distance between the patient's surgery target region and the surgical instrument held by them. If the surgeon cannot recognize the distance between the patient's surgery target region and the surgical instrument held by them, they may make critical mistakes such as injuring other regions on the periphery of the surgery target region. According to the present invention, it is possible to reduce the risk of such mistakes involved in the surgery.

(2) The control unit 102 creates the three-dimensional CT image by overlaying the CT slice images of the patient's surgery target region shot before the surgery, creates the three-dimensional MRI image by overlaying the MRI slice images of the patient's surgery target region shot before the surgery, and aligns and superimposes the three-dimensional CT image, the three-dimensional MRI image, and the prepared three-dimensional model image of the surgery target region to create the three-dimensional image of the patient's surgery target region. The control unit 102 then aligns and superimposes the created three-dimensional image of the patient's surgery target region and the frames of the microscope video acquired from the surgical microscope 200 to convert the microscope video into the three-dimensional video. In this manner, using the CT slice images, the MRI slice images, and the three-dimensional model image makes it possible to create the high-accuracy three-dimensional image and convert the microscope video into the three-dimensional video.

(3) The control unit 102 determines the coordinate value of the front end position of the surgical instrument in the microscope coordinate system, and converts the same into the coordinate value in the display coordinate system to determine the front end position of the surgical instrument in the three-dimensional video. Accordingly, the front end position of the surgical instrument seen in the microscope video can also be determined in the three-dimensional video.

(4) Based on the preset coordinate value of the surgery target region and the determined coordinate value of the front end position of the surgical instrument in the three-dimensional video, the control unit 102 calculates the linear distance, the distance in the depth direction, that is, in the depth direction, and the distance in the side-to-side direction, that is, in the horizontal direction, and the distance in the top-to-bottom direction, that is, in the vertical direction between the surgery target region and the front end position of the surgical instrument. This allows the surgeon to recognize the information on the distance between the current front end position of the surgical instrument and the surgery target region in the three-dimensional video.

(5) The control unit 102 displays the information indicating the position of the surgery target region in the three-dimensional video. This allows the surgeon to recognize the surgery target region in the three-dimensional video.

(6) The control unit 102 displays the information indicating the positions of the risky regions at risk for injury at the periphery of the surgery target region in the three-dimensional video. This allows the surgeon to recognize the risky regions at the periphery of the surgery target region with reduced risks involved in the surgery.

MODIFICATION EXAMPLES

The medical microscope system 10 in the embodiment described above can be modified in such a manner as described below.

(1) In the embodiment described above, along with the calibration process, the surgical instrument is placed on the observation target surface 3a to determine the length L of the surgical instrument in the microscope video during the calibration process. Then, when the position of the marking in the darkest color applied to the surgical instrument cannot be identified to determine the front end position of the surgical instrument, the front end position of the surgical instrument in the microscope video is estimated based on the length L of the surgical instrument. In the embodiment described above, the length L of the surgical instrument is calculated based on the surgical instrument placed on the observation target surface 3a during the calibration process. However, during the surgery, the surgical instrument may not be seen horizontally relative to the observation target surface. When the surgical instrument is seen with an inclination relative to the observation target surface in the microscope video, the length of the surgical instrument in the microscope video is different from the length L of the surgical instrument measured during the calibration process. In this case, the markings applied at equal spaces to the surgical instrument are seen more narrowly in the microscope video with increasing distance from the optical axis. In addition, the widths of the markings, that is, the longitudinal lengths of the markings illustrated in FIG. 4 become narrower with increasing distance from the optical axis in the microscope video. Accordingly, the control unit 102 may correct the length of the surgical instrument in the microscope video based on changes in the spaces between the markings and changes in the widths of the markings.

Specifically, the control unit 102 determines the spaces between the two each adjacent markings of the three consecutive markings in the microscope video, and calculates the ratio between these spaces. For example, out of the three consecutive markings 4b, 4c, and 4d illustrated in FIG. 4, the control unit 102 determines a space A between the markings 4b and 4c and a space B between the markings 4c and 4d, and calculates the ratio between the space A and the space B. This ratio indicates an inclination width in the Z-axis direction in the microscope coordinate system. Accordingly, the control unit 102 can calculate by a trigonometric function the length of the surgical instrument in the microscope video based on the length L of the surgical instrument measured during the calibration process and the inclination width, and correct the same.

Alternatively, the control unit 102 may calculate the ratio between the marking widths of the two adjacent markings. For example, taking the markings 4b and 4c illustrated in FIG. 4, the control unit 102 calculates the ratio between the width of the marking 4b and the width of the marking 4c. This ratio also indicates the inclination width in the Z-axis direction in the microscope coordinate system. Accordingly, the control unit 102 may also calculate by a trigonometric function the length of the surgical instrument in the microscope video based on the length L of the surgical instrument measured during the calibration process and the inclination width, and correct the same.

(2) In the embodiment described above, the plurality of markings 4a to 4f is applied to the surgical instrument, and the markings are color-coded to discriminate between the front end side and the back end side of the surgical instrument. However, the materials applied to the surgical instrument to discriminate between the front end side and the back end side of the surgical instrument may not be necessarily the markings. For example, to discriminate between the front end side and the back end side of the surgical instrument, numbers may be applied or arrows indicating the direction toward the front end side may be applied at the positions of the markings 4a to 4f illustrated in FIG. 4.

The present invention is not limited to the configuration of the foregoing embodiment as far as the characteristic functions of the present invention are not impaired. The foregoing embodiment may be combined with a plurality of modification examples.

The disclosure of the following basic application for priority is incorporated herein by reference:

Japanese Patent Application No. 246968 (applied on Nov. 29, 2013)

The invention claimed is:

1. A microscope video processing device comprising:
a microscope video acquisition unit that acquires a microscope video output from a surgical microscope at a predetermined frame rate;
a video conversion unit that converts the microscope video acquired by the microscope video acquisition unit into a three-dimensional video;
a surgical instrument position determination unit that, in a surgical instrument with a handle portion to which color-coded markings are applied at an equal interval to discriminate between the front end side and back end side of the surgical instrument in the microscopic video acquired by the microscope video acquisition unit, determines the position of a marking for identifying the foremost end position as front end position of the surgical instrument, and converts a coordinate value of the determined front end position in the microscope video into a coordinate value in the three-dimensional video to determine the front end position of the surgical instrument in the three-dimensional video converted by the video conversion unit;
a distance calculation unit that calculates a distance between a preset patient's surgery target region and the front end position of the surgical instrument determined by the surgical instrument position determination unit; and
a video output unit that outputs to a display unit an output video in which distance information indicative of the distance calculated by the distance calculation unit is displayed in the three-dimensional video,
wherein the video conversion unit creates a three-dimensional CT image by overlaying CT slice images of the patient's surgery target region shot before the surgery, creates a three-dimensional MRI image by overlaying MRI slice images of the patient's surgery target region shot before the surgery, aligns and superimposes the three-dimensional CT image, the three-dimensional MRI image, and a prepared three-dimensional model image of the surgery target region to create a three-dimensional image of the patient's surgery target region, and aligns and superimposes the three-dimensional image of the patient's surgery target region and frames of the microscope video acquired by the microscope video acquisition unit to convert the microscope video into the three-dimensional video.

2. A microscope video processing device comprising:
a microscope video acquisition unit that acquires a microscope video output from a surgical microscope at a predetermined frame rate;
a video conversion unit that converts the microscope video acquired by the microscope video acquisition unit into a three-dimensional video;
a surgical instrument position determination unit that, in a surgical instrument with a handle portion to which color-coded markings are applied at an equal interval to discriminate between the front end side and back end side of the surgical instrument in the microscopic video acquired by the microscope video acquisition unit, determines the position of a marking for identifying the foremost end position as front end position of the surgical instrument, and converts a coordinate value of the determined front end position in the microscope video into a coordinate value in the three-dimensional video to determine the front end position of the surgical instrument in the three-dimensional video converted by the video conversion unit;
a distance calculation unit that calculates a distance between a preset patient's surgery target region and the front end position of the surgical instrument determined by the surgical instrument position determination unit; and
a video output unit that outputs to a display unit an output video in which distance information indicative of the distance calculated by the distance calculation unit is displayed in the three-dimensional video,
wherein the distance calculation unit calculates a distance, a horizontal distance, a vertical distance, and a distance in a depth direction between the surgery target region and the front end positon of the surgical instrument, based on the preset coordinate value of the surgery target region in the three-dimensional video and the coordinate value of the front end position of the surgical instrument determined by the surgical instrument position determination unit.

3. The microscope video processing device according to claim 1, wherein, when the coordinate value of the front end position of the surgical instrument is not determined because the front end position of the surgical instrument is not seen in the microscope video acquired by the microscope video acquisition unit, the surgical instrument position determination unit estimates the coordinate value of the front end position of the surgical instrument based on part of the surgical instrument seen in the microscope video and a predetermined length of the surgical instrument.

4. The microscope video processing device according to claim 1, further comprising a surgical target region position information display unit that displays surgical target region position information indicating the position of the surgical target region in the three-dimensional video.

5. The microscope video processing device according to claim 1, further comprising a risky region position information display unit that displays risky region position information indicating risky regions at risk for injury on the periphery of the surgical target region in the three-dimensional video.

6. A medical microscope system comprising:
the microscope video processing device according to claim 1; and
a surgical microscope that is connected to the microscope video processing device to input a microscope video to the microscope video processing device at a predetermined frame rate.

7. The microscope video processing device according to claim 2, wherein, when the coordinate value of the front end position of the surgical instrument is not determined because the front end position of the surgical instrument is not seen in the microscope video acquired by the microscope video acquisition unit, the surgical instrument position determination unit estimates the coordinate value of the front end position of the surgical instrument based on part of the surgical instrument seen in the microscope video and a predetermined length of the surgical instrument.

8. The microscope video processing device according to claim 2, further comprising a surgical target region position information display unit that displays surgical target region position information indicating the position of the surgical target region in the three-dimensional video.

9. The microscope video processing device according to claim 2, further comprising a risky region position information display unit that displays risky region position information indicating risky regions at risk for injury on the periphery of the surgical target region in the three-dimensional video.

10. A medical microscope system comprising:
the microscope video processing device according to claim 2; and
a surgical microscope that is connected to the microscope video processing device to input a microscope video to the microscope video processing device at a predetermined frame rate.

* * * * *